(12) United States Patent
House

(10) Patent No.: US 7,662,146 B2
(45) Date of Patent: Feb. 16, 2010

(54) INDWELLING URINARY CATHETERIZATION ASSEMBLY

(75) Inventor: Jamie Glen House, Colorado Springs, CO (US)

(73) Assignee: Colorado Catheter Company, Inc., Colorado Springs, CO (US)

( * ) Notice: Subject to any disclaimer, the term of this patent is extended or adjusted under 35 U.S.C. 154(b) by 101 days.

(21) Appl. No.: 11/652,528

(22) Filed: Jan. 12, 2007

(65) Prior Publication Data

US 2007/0225687 A1 Sep. 27, 2007

Related U.S. Application Data

(60) Provisional application No. 60/780,972, filed on Mar. 10, 2006.

(51) Int. Cl.
*A61M 25/10* (2006.01)
*A61M 29/00* (2006.01)
(52) U.S. Cl. .......... 604/544; 604/103.05; 604/104; 604/915
(58) Field of Classification Search ........... 604/103.05, 604/317, 544, 915
See application file for complete search history.

(56) References Cited

U.S. PATENT DOCUMENTS

| 1,120,549 | A | * | 12/1914 | Schellberg | 604/171 |
|---|---|---|---|---|---|
| 2,009,825 | A | * | 7/1935 | Wappler | 604/171 |
| 3,345,988 | A | * | 10/1967 | Vitello | 604/172 |
| 3,421,509 | A | * | 1/1969 | Fiore | 604/171 |
| 3,606,889 | A | * | 9/1971 | Arblaster | 604/171 |
| 3,683,928 | A | * | 8/1972 | Kuntz | 604/171 |
| 3,853,130 | A | * | 12/1974 | Sheridan | 604/171 |
| 3,854,483 | A | * | 12/1974 | Powers | 604/172 |
| 3,894,540 | A | * | 7/1975 | Bonner, Jr. | 604/171 |
| 3,934,721 | A | * | 1/1976 | Juster et al. | 206/364 |
| 3,937,220 | A | * | 2/1976 | Coyne | 604/119 |
| 4,062,363 | A | * | 12/1977 | Bonner, Jr. | 604/171 |
| 4,178,735 | A | * | 12/1979 | Jackson | 53/473 |
| 4,327,723 | A | * | 5/1982 | Frankhouser | 604/171 |
| 4,327,735 | A | * | 5/1982 | Hampson | 604/171 |
| 4,392,853 | A | * | 7/1983 | Muto | 604/171 |
| 4,540,404 | A | * | 9/1985 | Wolvek | 604/103.05 |
| 4,551,137 | A | * | 11/1985 | Osborne | 604/171 |
| 4,571,239 | A | * | 2/1986 | Heyman | 604/544 |
| 4,622,033 | A |   | 11/1986 | Taniguchi |  |
| 4,634,433 | A | * | 1/1987 | Osborne | 604/171 |
| 4,652,259 | A | * | 3/1987 | O'Neil | 604/544 |
| 4,655,214 | A | * | 4/1987 | Linder | 128/207.18 |
| 4,710,169 | A | * | 12/1987 | Christopher | 604/104 |
| 4,738,666 | A | * | 4/1988 | Fuqua | 604/514 |
| 4,772,275 | A |   | 9/1988 | Erlich |  |
| 4,798,193 | A | * | 1/1989 | Giesy et al. | 600/114 |
| 4,811,847 | A | * | 3/1989 | Reif et al. | 206/571 |
| 4,834,710 | A |   | 5/1989 | Fleck |  |
| 5,149,326 | A |   | 9/1992 | Woodgrift et al. |  |
| 5,181,913 | A |   | 1/1993 | Erlich |  |
| 5,234,411 | A | * | 8/1993 | Vaillancourt | 604/171 |
| 5,239,981 | A | * | 8/1993 | Anapliotis | 600/122 |
| 5,242,398 | A |   | 9/1993 | Knoll et al. |  |
| 5,306,241 | A | * | 4/1994 | Samples | 604/544 |
| 5,334,153 | A | * | 8/1994 | McIntyre et al. | 604/99.02 |

(Continued)

*Primary Examiner*—Tatyana Zalukaeva
*Assistant Examiner*—Paula L Craig
(74) *Attorney, Agent, or Firm*—Moazzam & Associates, LLC

(57) ABSTRACT

An indwelling urinary catheter assembly is disclosed having an indwelling catheter and a sheath enclosing an insertable portion of the indwelling catheter.

23 Claims, 7 Drawing Sheets

U.S. PATENT DOCUMENTS

| | | | |
|---|---|---|---|
| 5,582,599 A * | 12/1996 | Daneshvar | 604/263 |
| 5,715,815 A * | 2/1998 | Lorenzen et al. | 128/207.14 |
| 5,779,670 A | 7/1998 | Bidwell et al. | |
| 5,779,671 A * | 7/1998 | Ressemann et al. | 604/164.13 |
| 5,792,114 A | 8/1998 | Fiore | |
| 5,895,374 A | 4/1999 | Rodsten | |
| 6,007,521 A * | 12/1999 | Bidwell et al. | 604/264 |
| 6,053,905 A | 4/2000 | Daignault et al. | |
| 6,059,107 A | 5/2000 | Nosted et al. | |
| 6,090,075 A | 7/2000 | House | |
| 6,176,849 B1 | 1/2001 | Yang et al. | |
| 6,217,569 B1 | 4/2001 | Fiore | |
| 6,409,717 B1 | 6/2002 | Israelsson et al. | |
| 6,471,684 B2 | 10/2002 | Dulak et al. | |
| 6,578,709 B1 | 6/2003 | Kavanagh et al. | |
| 6,602,244 B2 | 8/2003 | Kavanagh et al. | |
| 6,634,498 B2 | 10/2003 | Kayerod et al. | |
| 6,673,053 B2 | 1/2004 | Wang et al. | |
| 6,736,805 B2 | 5/2004 | Israelsson et al. | |
| 6,848,574 B1 | 2/2005 | Israelsson et al. | |
| 2001/0001443 A1 | 5/2001 | Kayerod et al. | |
| 2001/0007060 A1 | 7/2001 | Fiore | |
| 2001/0027295 A1 | 10/2001 | Dulak et al. | |
| 2001/0027299 A1 | 10/2001 | Yang et al. | |
| 2002/0169438 A1 * | 11/2002 | Sauer | 604/544 |
| 2003/0018302 A1 | 1/2003 | Kavanagh et al. | |
| 2004/0074794 A1 | 4/2004 | Conway et al. | |
| 2004/0153051 A1 | 8/2004 | Israelsson et al. | |
| 2004/0256264 A1 | 12/2004 | Israelsson et al. | |
| 2005/0015076 A1 | 1/2005 | Giebmeyer et al. | |
| 2005/0085841 A1 * | 4/2005 | Eversull et al. | 606/190 |
| 2005/0109648 A1 | 5/2005 | Kerzman et al. | |
| 2005/0137582 A1 | 6/2005 | Kull-Osterlin et al. | |
| 2006/0025753 A1 | 2/2006 | Kubalak et al. | |
| 2007/0049907 A1 * | 3/2007 | Fischer et al. | 604/544 |
| 2007/0161971 A1 * | 7/2007 | House | 604/544 |
| 2007/0225649 A1 * | 9/2007 | House | 604/171 |
| 2008/0091136 A1 * | 4/2008 | House | 604/23 |
| 2008/0097411 A1 * | 4/2008 | House | 604/544 |
| 2008/0147049 A1 * | 6/2008 | House et al. | 604/544 |
| 2008/0171973 A1 * | 7/2008 | House | 604/93.01 |
| 2008/0172042 A1 * | 7/2008 | House | 604/544 |

* cited by examiner

INDWELLING URINARY CATHETERIZATION ASSEMBLY

This application claims priority to U.S. Provisional Patent Application Ser. No. 60/780,972, filed Mar. 10, 2006, the content of which is hereby incorporated by reference in its entirety into this disclosure.

BACKGROUND OF THE INVENTION

1. Field of the Invention

The present disclosure is directed to devices and methods for catheterization of the urinary bladder. More particularly, the present invention relates to devices and methods for extended or long-term catheterization of the urinary bladder.

2. Background of the Invention

The occasional or periodic catheterization of an individual's urinary bladder is a common practice today for many persons who are in a hospital setting, a nursing home, doctor's office, rehabilitation facility, or at home. For instance, a patient may be catheterized to treat such conditions as urinary retention, the inability to evacuate urine, or for the purpose of obtaining a sterile urine specimen from a patient in a doctor's office. Some catheterizations may be intermittent or repeated, while other catheterizations may be extended, or long-term. Extended catheterizations may require the use of an indwelling (e.g., "Foley") catheter.

Generally, catheterizations may be assisted (non self-catheterizations) or unassisted (self-catheterizations). In assisted catheterizations, it is commonplace for a nurse to perform the catheterization procedure using pre-assembled kits, or catheterization tray ("cath tray"), which typically includes a catheter, a drape, disposable gloves, antiseptic solution, cotton balls, a sealed packet containing sterile lubricating jelly, forceps, waterproof absorbent underpad, prepping cotton balls, a sterile urine specimen bottle, and a urine collection container. In particular, for long-term catheterizations, the catheter provided in the cath tray is typically an indwelling catheter capable of being sufficiently maintained within the patient for an extended period of time. All of these items are typically packaged together and sterilized.

To perform the typical catheterization, the nurse opens the tray, dons sterile gloves and places the drape around the patient's genitalia. The antiseptic solution is opened and poured over the cotton balls. The packet of lubricating jelly is opened and squeezed onto a sterile field. The patient's urethral opening is cleansed with the saturated cotton balls, the nurse holding each with the forceps. The nurse then runs the tip end of the catheter, comprising the first inch or two (about 2.5 cm to about 5 cm) of the insertable portion, through the lubricating jelly. The catheter is then inserted into the urethra and advanced until urine begins to flow. The urine is drained into the urine collection container. A urine specimen may be caught in the specimen bottle, if needed. For long-term catheterizations, a band around the tip of the indwelling catheter may be expanded such that the catheter may not be easily pulled from the bladder and is thus sufficiently maintained in the patient for an extended period of time. This basic procedure is widely used in inpatient hospitals around the world, and has remained essentially the same for 50 years.

Although the catheterization kit may be sterile prior to opening, the nurse must open the tray and handle the various items in the tray in order to use the kit. Further, even if special precautions are taken, maintaining a "sterile" environment during the procedure may present challenges. Non-sterile techniques and/or contamination of the catheter may result in infection of the patient's urinary tract. In some instances, urinary tract infections may lead to morbidity and additional costs to the patient and society.

In addition to sanitation concerns, because multiple steps are involved to perform the procedure (e.g., sterilization, lubrication, insertion, etc.), a nurse may spend a significant amount of time (e.g., 10 minutes or more) carrying out each catheterization. Further, the "cath tray" procedure maybe expensive or otherwise impractical for use with some individuals and situations today.

A variety of catheterization kits and products are currently available. For instance, U.S. Pat. No. 6,090,075 (House I) discloses a catheterization kit including a catheter comprising a rigid introducer member for positioning catheter assembly against the urethral opening, a flexible catheter, and a flexible thin-walled sheath surrounding the catheter and partially covering the catheter introducer.

Some catheterization assemblies and kits employ hydrophilic catheters that are self-lubricating when wetted with a fluid (e.g., water) prior to use. U.S. Pat. No. 6,409,717 (Astra Aktiebolag) and U.S. Pat. No. 6,736,805 (AstraZeneca AB) describe apparatus for wetting a hydrophilic urinary catheter, comprising a wetting receptacle which defines a wetting fluid receiving area for receiving the catheter and a wetting fluid container having a discharge outlet movable from a closed position to an open position on application of a predetermined condition thereto to enable the wetting fluid to be discharged from the container. U.S. Pat. No. 6,634,498 (Coloplast A/S) describes certain urinary catheter assemblies including a urinary catheter having at least a part of its surface a hydrophilic surface layer intended to produce a low-friction surface character of the catheter by treatment with a liquid swelling medium during manufacture of the catheter assembly, and a catheter package having a cavity for accommodation of the catheter. The package includes a compartment having walls of a gas impermeable material that accommodates the liquid swelling medium, and a pre-treated catheter for long term preservation of the low-friction surface character and provision of a ready-to-use catheter assembly.

Some of the aforementioned catheter devices include a protective sheath that surrounds the catheter. Such a protective sheath may serve multiple purposes. For instance, the sheath may prevent contamination of catheter as the catheter is handled prior to and/or during use. In addition, in some hydrophilic catheters, the sheath may serve to contain a wetting agent used to lubricate the catheter during use. However, certain of the aforementioned catheter devices are intended for intermittent or short-term catheterizations and may not work adequately for long-term or extended catheterizations.

Accordingly, there remains a need for an easy-to-use, sanitary and disposable catheterization assembly for extended or long-term catheterizations.

SUMMARY OF THE INVENTION

An exemplary embodiment disclosed herein serves as an indwelling urinary catheter assembly. In certain embodiments, the indwelling catheter assembly comprises an indwelling catheter including a first end having a urine inlet, a second end having a urine outlet, a takeoff port having a port bore, an expander, and a urethra insertable portion. The urine inlet and urine outlet are in fluid communication, and the port bore and the expander are in fluid communication. In addition, the indwelling catheter assembly further comprises a pliable sheath comprising a lumen, wherein the sheath encloses all or part of the insertable portion.

The foregoing has broadly outlined certain features of the embodiments described herein in order that the detailed description that follows may be better understood. Additional features will be described hereinafter. It should be appreciated by those skilled in the art that the conception and the specific embodiments disclosed may be readily utilized as a basis for modifying or designing other devices, methods, or systems for carrying out the same purposes of the embodiments disclosed herein. It should also be realized by those skilled in the art that such equivalent constructions do not depart from the spirit and scope of the invention as set forth in the appended claims.

DETAILED DESCRIPTION OF THE INVENTION

Figure 1A:
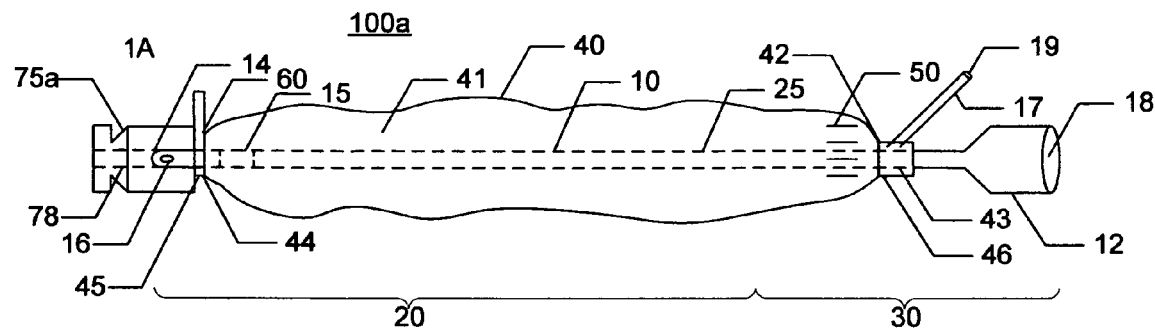
FIG. 1A is a side view of an embodiment of a sheathed indwelling catheter assembly.

The present invention provides for catheter and catheter assemblies capable of mating with adhesive pads in order to increase a catheterized patient's mobility and prevent movement of the catheter in and out (pistoning) of The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular system components. As one skilled in the art will appreciate, different persons may refer to a component by different names. This document does not intend to distinguish between components that differ in name but not function. The drawing figures are not necessarily to scale. Certain features of the invention may be shown exaggerated in scale or in somewhat schematic form, and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

Also, the term "distal" is intended to refer to positions relatively away from the patient when the catheter is in use, while the term "proximal" is intended to refer to positions relatively near the patient when the catheter is in use. Thus, the proximal end of a device is relatively near the patient as compared to the distal end of the device, which is relatively away from the patient.

U.S. Pat. No. 6,090,075 (House I), U.S. App. No. 60/708,893 (House II), and U.S. application Ser. No. 11/326,699 (House III), and U.S. Provisional Application U.S. Express Mail Label No. EV 303424660 US, filed concurrently herewith, are each hereby incorporated herein by reference in their entirety.

Referring to FIG. 1A, an embodiment of a sheathed indwelling catheter assembly 100a is shown. Assembly 100a comprises a flexible indwelling catheter 10 and a protective sheath 40. Catheter 10 includes a urethra insertable portion 20 (portion insertable into a patient's urethra) and a non-insertable portion 30 (portion not intended to be inserted into the patient). Insertable portion 20 commences at a catheter tip 14 and ends at an insertion stop location 25, adjacent non-insertable portion 30.

Catheter 10 further comprises one or more urine inlet(s) 16 in tip 14, a distal end 12 including a urine outlet 18, and a urine conduit 11 in fluid communication with inlet(s) 16 and outlet 18. In this configuration, when catheter 10 is sufficiently inserted into a patient's bladder, urine enters catheter 10 through inlet(s) 16, is conducted through urine conduit 11 of catheter 10, and exits catheter 10 at outlet 18. Optionally, a urine collection bag or receptacle may be coupled to outlet 18 such that urine may exit outlet 18 into the collection bag.

In addition, catheter 10 comprises a takeoff port 17 having a port bore 19, an expander conduit 13, and an expander 15. Port bore 19 is in fluid communication with expander 15 via expander conduit 13. As with many indwelling catheters, fluid (e.g., sterile water, saline solution, air, etc.) may be injected into port bore 19 via takeoff port 17 to fill and expand expander 15. In this manner, once catheter 10 is properly positioned in the bladder of the patient, expander 15 may be expanded (e.g., "ballooned") such that tip 14 of catheter 10 may be maintained within the patient's bladder for an extended period of time (e.g., tip 14 is not easily withdrawn from the patients bladder when expander 15 is expanded). Once the catheterization is no longer necessary, fluid may be withdrawn from expander 15 through port bore 19 and out of catheter 10, thereby reducing the size of expander 15 such that catheter 10 may be removed from the patient. Port bore 19, expander conduit 13, and expander 15 are not in fluid communication with inlet(s) 16, urine conduit 11, nor outlet 18. In other words, there is no mixing of fluids within expander conduit 13 and urine conduit 11. In select embodiments, takeoff port 17 is located in the distal $\frac{1}{3}^{rd}$ of catheter 10.

Figure 1B:
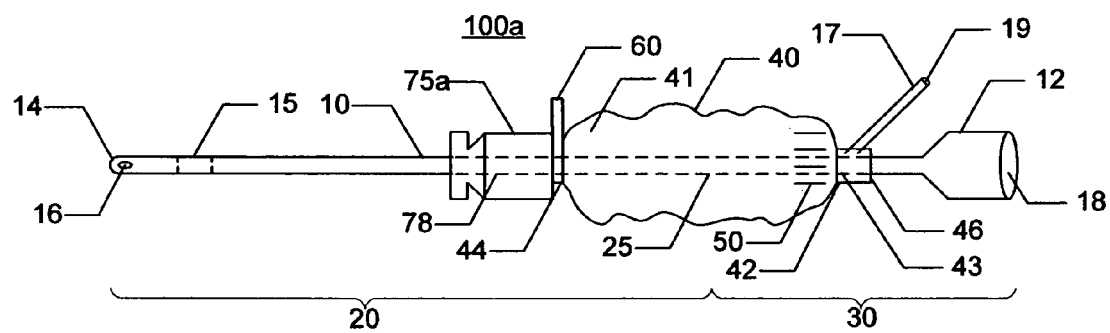
FIG. 1B is a side view of the sheathed indwelling catheter assembly of FIG. 1A, with the sheath partially gathered.
Figure 1C:
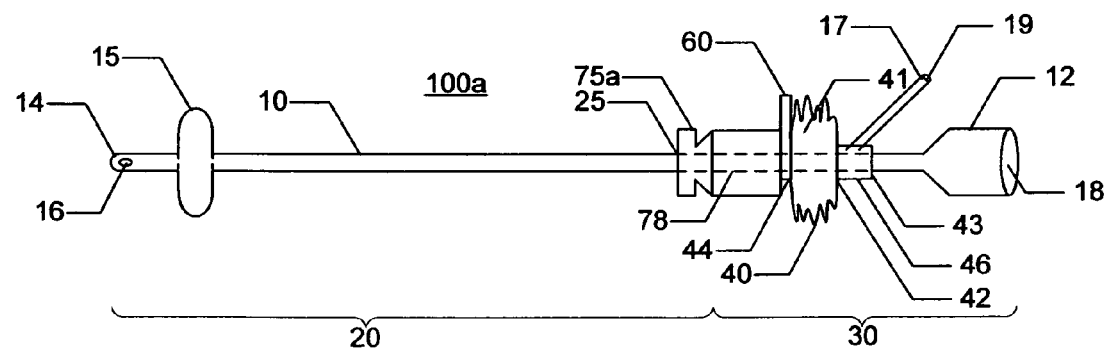
FIG. 1C is a side view of the sheathed indwelling catheter assembly of FIG. 1A, with the sheath substantially gathered.
Figure 1D:
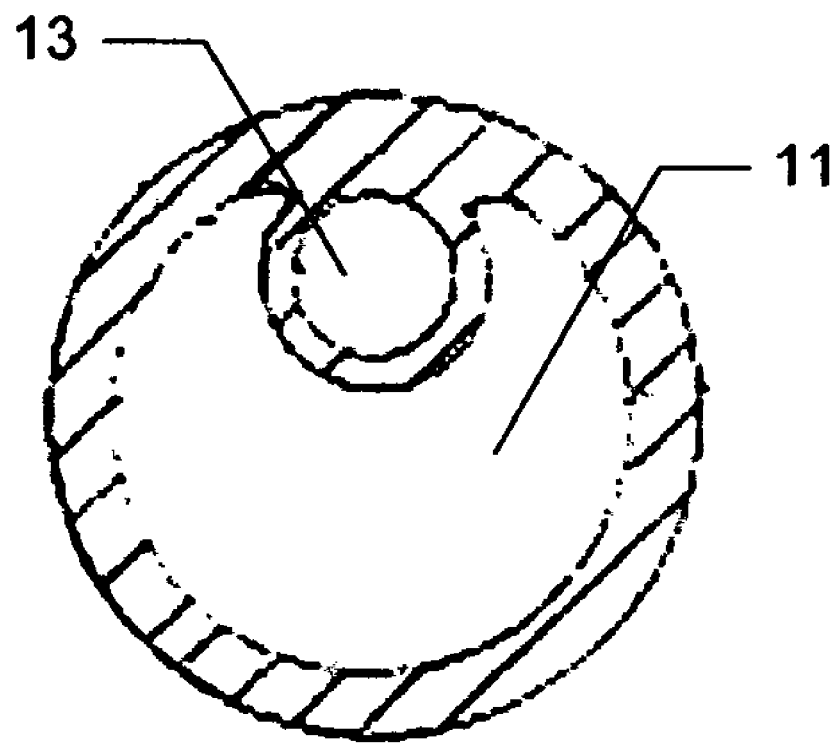
FIG. 1D is an enlarged cross-section of the indwelling catheter of FIG. 1A.

FIG. 1D shows an enlarged cross-section of catheter 10 taken between expander 15 and takeoff port 17. Expander conduit 13 allows fluid communication between expander 15 and port bore 19. Further, urine conduit 11 allows fluid communication between one or more inlet(s) 16 and urine outlet 12. However, as best seen in FIG. 1D, there is no fluid communication between urine conduit 11 and expander conduit 13.

Catheter 10 may be similar to conventional flexible indwelling catheters, sometimes referred to as "Foley" catheters. Catheter 10 may comprise any suitable material including without limitation, vinyl, red rubber latex, silicone elastomer, or the like.

Referring again to FIG. 1A, catheter tip 14 initially rests inside, and is supported by, an introducer 75a. In this embodiment, introducer 75a is an introducer similar to that disclosed in House II. However, in other embodiments, the introducer enclosing tip 14 may be any suitable device capable of preventing direct contact of tip 14 with non-sterile surfaces. Introducer 75a slidingly receives catheter 10. In particular, as best seen in FIGS. 1A-1C, tip 14 and insertable portion 20 are intended to slide through introducer 75a, thereby advancing insertable portion 20 into the patient's urethra. Introducer 75a includes a conduit or guide 78 that controls the direction of motion of catheter 10, including tip 14, relative to introducer 75a.

Sheath 40 comprises a first sheath terminus 44 and a second sheath terminus 42. First sheath terminus 44 comprises a first collar 45 coupled to introducer 75a. First sheath terminus 44 slidingly engages catheter 10. First collar 45 is fixed to introducer 75a by first collar 45 such that first collar 45 does not move rotationally or translationally relative to introducer 75a. In different embodiments, first sheath terminus may not comprise a collar. Moreover, in other embodiments, first sheath terminus 44 may not be fixed to introducer 75a or any other device that covers tip 14, if provided. Further, in certain embodiments, similar to that shown in FIGS. 2A and B, first sheath terminus 44 is removably coupled to an introducer. Still further, in some embodiments (e.g., FIG. 3A), first sheath terminus 44 completely encloses tip 14.

Still referring to FIGS. 1A-1C, in this embodiment second sheath terminus 42 comprises a second collar 46. Second collar 46 is coupled to catheter 10 at an attachment point 43. Attachment point 43 is provided between tip 14 and distal end 12. Second collar 46 is coupled to catheter 10 at attachment point 43, which straddles takeoff port 17. However, in general, second sheath terminus 42 (e.g., second collar 46) may be coupled to catheter 10 in any suitable location including without limitation, straddling takeoff port 17, between tip 14 and takeoff port 17, between takeoff port 17 and distal end 12, or other locations.

In the embodiment shown in FIGS. 1A-1C, second collar 46 is fixed to catheter 10 such that second collar 46 does not move rotationally or translationally relative to catheter 10. However, in general, second sheath terminus 42 (e.g., second collar 46) may be coupled to catheter 10 by any suitable means including without limitation, by heat fitting (e.g., partially melting second sheath terminus 42 to catheter 10) (e.g., FIG. 4E), by pressure fitting, by adhesive (e.g., glue), by a collar attached to second sheath terminus 42 and catheter 10 (e.g., FIG. 1A), or combinations thereof. In different embodiments (e.g., FIG. 4A), second sheath terminus 42 may slidingly engage catheter 10 at attachment point 43.

As shown in FIGS. 1A-1C, fixation tab 60 extends from first collar 45. In other embodiments, no fixation tab 60 is provided. In general, fixation tab 60 serves to couple catheter 10 to the patient once tip 14 is properly positioned in the patient's bladder. Fixation tab 60 is discussed in more detail below.

Sheath 40 encloses all, or at least part of, insertable portion 20, thereby creating a sheath lumen 41 between sheath 40 and catheter 10. Sheath 40 may comprise any suitable material. For example, sheath 40 may be an elongated, flexible plastic membrane, such as a bag. Further, sheath 40 and lumen 41 may comprise any suitable geometry including without limitation, rectangular, cylindrical, flattened, inflated, partially inflated, or combinations thereof.

Together, introducer 75a (or other device covering tip 14) and sheath 40 cooperate to enclose and protect insertable portion 20 of catheter 10 from contamination prior to and during use. In the embodiment shown in FIG. 1A, insertable portion 20 of catheter 10 is maintained in sterile condition inside introducer 75a and sheath 40. In embodiments where no introducer 75a, or other device covering tip 14, is provided (e.g., FIG. 3A), insertable portion 20 of catheter 10 may be fully enclosed within sheath 40 and thereby maintained in sterile condition.

The urethra-insertable portion 20 of catheter 10 is generally the length of catheter that may be appropriately inserted into the patient's urethra in order to perform a successful catheterization to drain the patient's urinary bladder. In select embodiments, insertable portion 20 is about $\frac{2}{3}^{rd}$ the length of catheter 10. The actual length of catheter 10, and the length of the insertable portion 20, may depend on the application (e.g., adult or child size) and may also vary somewhat from one patient to another. As a practical matter, insertable portion 20 is decreased, at least to some extent, by the distance on catheter 10 required to accommodate introducer 75a (if provided) and sheath 40 when sheath 40 is gathered toward second sheath terminus 42.

As discussed below in more detail (see "Catheterization Procedure"), during use of assembly 100a, flexible sheath 40 is gathered toward second sheath terminus 42 in order to advance tip 14 and insertable portion 20 into the patient's urethra Thus it can be readily appreciated that, in some embodiments, less than all of catheter 10 protected by the sheath 40 may be needed for insertion into the patient. Accordingly, an insertion stop location 25 (where the catheter stops near the urethral opening upon establishment of urine flow) may substantially coincide with attachment point 43, or it may be spaced away from attachment point 43 (e.g., closer to tip 14).

FIG. 1A shows the urethra-contacting end of assembly 100a (proximal end of assembly 100a) as including an introducer 75a. However, in general, the proximal end of assembly 100a may comprise any suitable configuration. For example, in some embodiments, introducer 75a may be replaced with another type of introducer or tip cover to keep sterile at least the insertable portion 20 of the catheter 10 prior to insertion. In other embodiments, introducer 75a or other tip cover may be similar to those that are known in the art. For example, the introducer may comprise an O'Neil® type introducer with "cross-cut" end (e.g., FIG. 2A-2C) or an introducer similar to that disclosed in House II. Embodiments of an O'Neil® type introducer are disclosed in U.S. Pat. No. 4,652,259, which is hereby incorporated herein by reference in its entirety. Further, introducer 75a or other tip cover may be removable from catheter 10 and/or slidingly engage catheter 10 (e.g., be slid toward distal end 12 to advance insertable portion 20 as shown in FIGS. 1B and C). Still further, in some embodiments (e.g., FIG. 3A), catheter 10 may be provided without introducer 75a or other tip cover, and sheath 40 may completely or partially enclose insertable portion 20 of catheter 10. Additional suitable configurations for the proximal end of assembly 100a are disclosed in House I, House II, and House III, which are each hereby incorporated by reference in their entirety.

In use, it may be desirable to lubricate tip 14 and a proximal portion insertable portion 20 prior to advancing tip 14 into the patient's urethra. Thus, in some embodiments, introducer 75a (or other protective tip cover) and/or lumen 41 of sheath 40 may contain a lubricant, or a wetting agent in the case of a hydrophilic indwelling catheter. Alternatively, tip 14 and a proximal portion of insertable portion 20 may be lubricated by applying a sterile lubricating gel.

Still referring to FIGS. 1A-1C, during use, a nurse may grasp introducer 75a and/or catheter 10 through flexible sheath 40 near the tip end 14 and align the catheter tip 14 with the patient's urethra. The nurse may then push tip 14 through introducer 75a and advance catheter tip 14 into the patient's urethra. In embodiments that do not include an introducer 75a or other tip cover (e.g., FIGS. 3A and B), a portion of sheath 40 near tip 14 may need to be opened to allow catheter tip 14 to emerge.

Sheath 40 is gathered toward distal end 12 to further advance catheter tip 14, giving catheter assembly 100a an appearance similar to that shown in FIG. 1B. As the catheter tip 14 is advanced by the nurse, a portion of sheath 40 becomes gathered toward second sheath terminus 42. By appropriately repositioning the nurse's grasp on introducer 75a and/or catheter 10 through sheath 40, and continuing to gently urge the insertable-portion 20 of catheter 10 in the patient's urethra, sheath 40 may continue to be gathered toward distal end 12, giving catheter assembly 100a an appearance similar to that shown in FIG. 1C. When the catheter tip enters the patient's bladder a sufficient distance to commence optimal draining of accumulated urine (e.g., about 1 cm), further insertion of insertable portion 20 ceases. At this point, the nurse may inflate expander 15 by injecting a fluid (e.g., sterile water, saline solution) into port bore 19 provided in takeoff port 17. In some embodiments, expander 15 may be inflated by injecting 5-10 cc of fluid. Once expander 15 is inflated, as best seen in FIG. 1C, to facilitate proper retention of catheter 10 in the patient's urethra for an extended period of time. Further, once tip 14 is properly positioned within the patient's bladder for extended catheterization, fixation tab 60 may be coupled to the patient. By coupling fixation tab 60 to the patient, catheter 10 may be maintained in a proper orientation, and further, introducer 75a and sheath 40 may be maintained in the gathered position shown in FIG. 1C. A urine collection bag or receptacle (not shown) may be employed to provide storage for drained urine.

Thus, introducer 75a and sheath 40 cooperate to protect insertable portion 20 from contamination prior to and during use. For example, before use, introducer 75a and sheath 40 completely enclose insertable portion 20 of catheter 10. In addition, during use, introducer 75a and sheath 40 are pulled back by the nurse as insertable portion 20 is advanced into the patient, without the need for the nurse to directly contact insertable portion 20, the nurse instead grasping the portion of catheter 10 that is enclosed within sheath 40. By deterring contamination, introducer 75a and sheath 40 may reduce the occurrences of urinary tract infections in patients. Further, by using introducer 75a and sheath 40 to maintain a sterile catheter, the need for separate antiseptic solutions, cotton balls, forceps and other devices conventionally used to maintain the sterility of an indwelling catheter may be eliminated. By eliminating these additional items required to maintain sterility of an indwelling catheter, embodiments of the sheathed indwelling catheter assembly described herein are intended to reduce the cost for indwelling catheter kits, reduce the time required to perform an indwelling catheterization, and reduce urinary tract infections.

In some catheter assemblies, the process of gathering sheath 40 to advance insertable portion 20 may result in an increase in pressure (e.g., a pressure build-up) in lumen 41. This may particularly be a problem with catheter assemblies in which there is limited or no means to relieve pressure build-up within lumen 41 (e.g., no fluid communication between lumen 41 and the environment outside sheathed catheter assembly 100a). Without being limited by theory, as the flexible sheath 40 is gathered, the volume of lumen 41 may decrease. In embodiments in which lumen 41 is not in fluid communication with a collection bag or an environment outside sheath 40, some fluid contained within lumen 41 (e.g., air, wetting agent, etc.) may become trapped and compressed, resulting in a pressure buildup within lumen 41 (e.g., sheath 40 may "balloon-up"). Excessive pressure buildup within lumen 41 may result in undesirable consequences. For instance, excessive pressure in lumen 41 may create forces tending to push introducer 75a towards tip 14, thereby limiting the degree to which the catheter may be advanced into the urethra. In addition, pressure build-up may cause sheath 40 to "balloon up," thereby detrimentally affecting the ability of the user to grasp the catheter 10 through the sheath 40. To help relieve pressure build-up within lumen 41, one or more vents 50 may be provided in assembly 100a as shown in FIG. 1A. Vents 50 are in fluid communication with lumen 40 and an environment outside sheath 41 and thus allow compressed fluid (e.g., air) within lumen 41 to escape lumen 41. In the embodiment shown in FIGS. 1A-1C, vents 50 are provided in sheath 40. However, in other embodiments, vents 50 may be provided in any suitable location including without limitation, sheath 40, first sheath terminus 44, second sheath terminus 42, introducer 75a, or combinations thereof. Still further, although vents 50 shown in FIG. 1A are slits, vents 50 may be any suitable geometry including without limitation slits, perforations, holes, pores, or combinations thereof. Vents 50 are preferably located adjacent second sheath terminus 42 in the region of non-insertable portion 30, such that any possible contamination of catheter 10 via vents 50 will occur as far from insertable portion 30 as possible. Additional suitable embodiments of vents are disclosed in U.S. Provisional Patent Application EV 303424660 US.

Figure 2A:
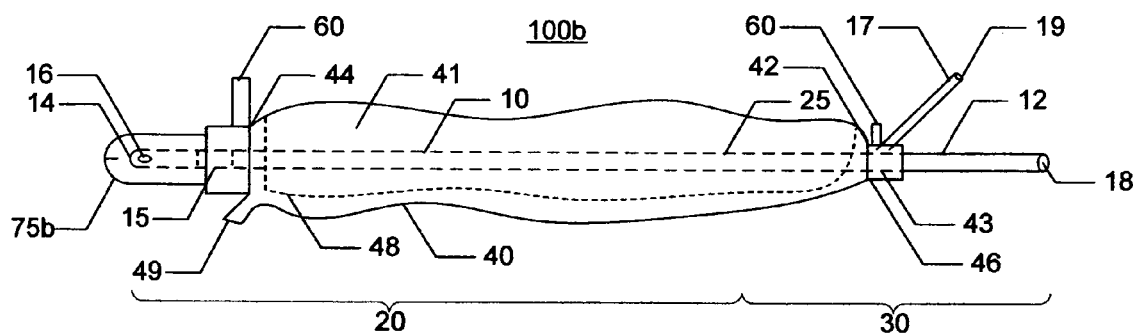
FIG. 2A is a side view of another embodiment of a sheathed indwelling catheter assembly.

Referring to FIG. 2A, another embodiment of a sheathed indwelling catheter assembly 100b is illustrated. Assembly 100b comprises a flexible indwelling catheter 10 and a protective sheath 40. Indwelling catheter 10 includes a urethra insertable portion 20 and a non-insertable portion 30. Insertable portion 20 commences at a catheter tip 14 and ends at an insertion stop location 25, adjacent non-insertable portion 30. Catheter 10 may be similar to conventional flexible indwelling catheters.

Figure 2B:
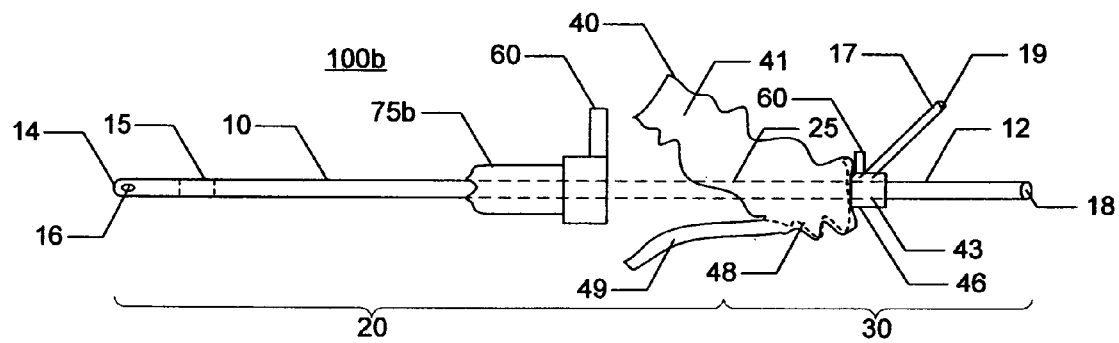
FIG. 2B is a side view of the sheathed indwelling catheter assembly of FIG. 2A, with the sheath partially gathered and partially removed.
Figure 2C:
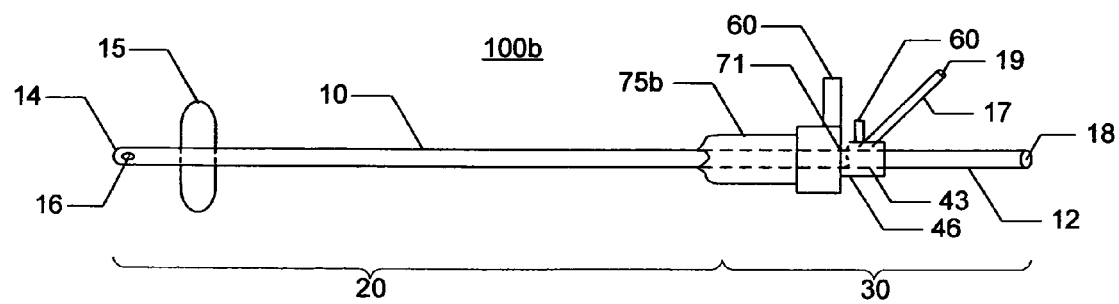
FIG. 2C is a side view of the sheathed indwelling catheter assembly of FIG. 2A, with the sheath completely removed.

Catheter tip 14 initially rests inside, and is supported by, an introducer 75b. In this embodiment, introducer 75b is similar to an O'Neil® type introducer. However, in other embodiments, the proximal end of catheter 10 may be enclosed or covered by another type of introducer (e.g., introducer 75a in FIG. 1A), a removable tip cover, or the like. As shown in FIGS. 2A-2C, introducer 75b slidingly engages catheter 10. In particular, introducer 75b is intended to slide along insertable portion 20, thereby exposing insertable portion 20 such that it may be inserted and advanced into the urethra of the patient. Introducer 75b may include a guide to aid in aligning tip 14 and controlling the direction of catheter 10, including tip 14.

Sheath 40 comprises a first sheath terminus 44 and a second sheath terminus 42. First sheath terminus 44 is removably coupled to introducer 75. Second sheath terminus 42 is removably coupled to a second collar 46. Second collar 46 is coupled to catheter 10 at attachment point 43. Attachment point 43 is provided between tip 14 and distal end 12. In particular, attachment point 43 is positioned about takeoff port 17 such that second collar 46 straddles takeoff port 17. By straddling takeoff port 17, second collar 46 is effectively fixed to catheter 10 such that second collar 46 does not move rotationally or translationally relative to catheter 10. In general, second sheath terminus 42 may be coupled to catheter 10 by any suitable means, including without limitation, by heat fitting (e.g., partially melting second sheath terminus 42 to catheter 10), by pressure fitting, by adhesive (e.g., glue), by a collar attached to second sheath terminus 42 and catheter 10, or combinations thereof.

A fixation tab 60 extends from introducer 75b. Further a second fixation tab 60 extends from second collar 46. In other embodiments, no fixation tab 60 is provided. In general, fixation tab 60 serves to couple catheter 10 to the patient once tip 14 is properly positioned in the patient's bladder. Fixation tab 60 is discussed in more detail below.

Sheath 40 encloses all, or at least part of, insertable portion 20, thereby creating a sheath lumen 41 between sheath 40 and catheter 10. Sheath 40 may comprise any suitable material (e.g., flexible plastic material, flexible fabric material, or the like). Further, sheath 40 and lumen 41 may comprise any suitable geometry including without limitation, rectangular, cylindrical, flattened, inflated, partially inflated, or combinations thereof.

In the embodiment shown in FIGS. 2A and 2B, sheath 40 further comprises a pull tab 49 associated with a tear line 48. Pull tab 49 may be provided at any suitable position on sheath 40, however, preferably pull tab 49 is positioned near the proximal end of sheath 40. Tear line 48 may be a pre-weakened (e.g., very thin, slightly perforated, etc.) line along sheath 40 that is intentionally provided therein to permit the sheath to tear under a slight to moderate force. Tear line 48 is intended to tear as pull tab 49 is pulled away from sheath 40. In particular, tear line 48 is intended to tear under force applied to pull tab 49 before any other region of sheath 40 tears. Tearing sheath 40 along tear line 48 permits sheath 40 to be removed from its position disposed about catheter 10.

Together, introducer 75b and sheath 40 cooperate to enclose and protect insertable portion 20 of catheter 10 from contamination prior to and during use. In the embodiment shown in FIG. 2A, insertable portion 20 of catheter 10 is maintained in sterile condition inside introducer 75b and sheath 40.

As discussed above, the urethra-insertable portion 20 of catheter 10 is generally the length of catheter that may be appropriately inserted into the patient's urethra in order to perform a successful catheterization to drain the patient's urinary bladder. As a practical matter, insertable portion 20 is decreased, at least to some extent, by the distance on catheter 10 required to accommodate introducer 75b, if provided, as introducer 75b is gathered towards second collar 46. In different embodiments, the introducer (e.g., introducer 75a, introducer 75b) or other tip cover may be designed to be completely removed from catheter 10 such that the introducer or tip cover does not take up space on catheter 10. For example, the introducer may be designed to be a "breakaway" introducer. In addition, in the embodiment shown in FIGS. 2A-2C, gathering sheath 40 towards distal end 12 does not have the effect of decreasing or limiting the length of catheter 10 serving as insertable portion 20 because sheath 40 may be removed from catheter 10 as it is gathered toward second collar 46 (see FIGS. 2B and 2C).

FIGS. 2A-2C show the urethra-contacting end of assembly 100b (proximal end of catheter 10) as including an introducer 75b. However, in general, the proximal end of catheter 10 may comprise any suitable configuration. In some embodiments, introducer 75b may be similar to those that are known in the art. For example, in some embodiments the proximal end of catheter 10 may be enclosed or covered by an introducer similar to that disclosed in FIG. 1A or other type of protective tip cover capable of keeping at least the insertable portion of the catheter sterile prior to and during use.

As discussed above, in use, it may be desirable to lubricate tip 14 and a proximal portion of insertable portion 20 prior to advancing tip 14 into the patient's urethra. Thus, in some embodiments, introducer 75b and/or lumen 41 of sheath 40 may contain a lubricant or wetting agent in the case of a hydrophilic indwelling catheter. Alternatively, a sterile lubricating gel may be applied to tip 14 and a proximal portion of insertable portion 20 prior to insertion.

Referring to FIGS. 2A-2C, during use, a nurse may grasp introducer 75b and align introducer 75b and catheter tip 14 with the patient's urethra. The nurse may then push the proximal tip of introducer 75b into the patient's urethra approximately 1-2 cm. Then the nurse may grasp catheter 10 through sheath 40 and advance tip 14 through introducer 75b and into the patient's urethra.

As insertable portion 20 is advanced into the patient's urethra, a portion of sheath 40 may become gathered toward second sheath terminus 42. At some point, the nurse may begin pulling on pull tab 49 to start tearing sheath 40 along tear line 48 as best illustrated in FIG. 2B. The nurse may begin tearing sheath 40 along tear line 48 when introducer 75b is positioned ⅓ to ½ the way down insertable portion 20, or when tip 14 is sufficiently in the patient's bladder.

By appropriately repositioning the nurse's grasp on introducer 75b and/or catheter 10 through sheath 40, and continuing to gently urge the insertable-portion 20 of catheter 10 into the patient's urethra, sheath 40 may continue to become gathered toward second sheath terminus 42. Periodically, the nurse may further pull pull tab 49 to continue tearing sheath 40 along tear line 48. When the catheter tip enters the patient's bladder a sufficient distance to commence optimal draining of accumulated urine (e.g., about 1 cm), further insertion of insertable portion 20 is halted. At this point, the nurse may inflate expander 15 by injecting a fluid (e.g., sterile water, saline solution) into port bore 19 provided in takeoff port 17. If sheath 40 has not been removed by this point, the nurse may remove the remainder of sheath 40 may be removed from catheter 10 by pulling on pull tab 49. Further, once tip 14 is properly positioned within the patient's bladder and sheath 40 is completely removed from catheter 10, introducer 75b may be secured in position adjacent collar 46 as illustrated in FIG. 2C. In some embodiments, introducer 75b may be coupled to second collar 46 at attachment point 71. In such embodiments, introducer 75b may be coupled to second collar 46 by any suitable means including without limitation, a locking mechanism, an adhesive, or combinations thereof. In addition, fixation tab 60 may be employed to couple catheter 10 to the patient. By coupling fixation tab 60 of introducer 75b to the patient, catheter 10 may be maintained in a proper orientation, and further introducer 75b may be maintained in gathered position shown in FIG. 2C.

Thus, introducer 75b and sheath 40 may prevent contamination of insertable portion 20 of indwelling catheter 10 prior to and during use. For example, before use, introducer 75b and sheath 40 completely enclose insertable portion 20 of catheter 10. In addition, during use, introducer 75b and sheath 40 are pulled back by the nurse as insertable portion 20 is advanced into the patient, without the need for the nurse to directly contact insertable portion 20. By deterring contamination, introducer 75b and sheath 40 may reduce the occurrences of urinary tract infections in patients. Further, by using introducer 75b and sheath 40 to maintain a sterile catheter, the need for separate antiseptic solutions, cotton balls, forceps and other devices conventionally used to sterilize an indwelling catheter may be eliminated. By eliminating these additional items required to maintain sterility of an indwelling catheter, embodiments of the sheathed indwelling catheter assembly described herein are intended to reduce the cost for indwelling catheter kits, reduce the time required to perform an indwelling catheterization, and reduce urinary tract infections.

As previously discussed, if pressure build-up within lumen 41 is a concern, vents in fluid communication with lumen 41 and the environment outside sheath 40 may be provided.

Figure 3A:
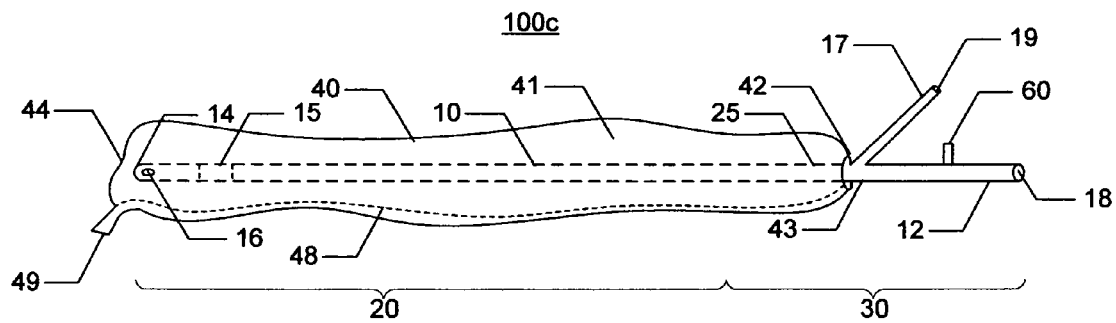
FIG. 3A is a side view of another embodiment of a sheathed indwelling catheter assembly.

Referring to FIG. 3A, another embodiment of a sheathed indwelling catheter assembly 100c is illustrated. Assembly 100c comprises a flexible indwelling catheter 10 and a protective sheath 40. Indwelling catheter 10 includes a urethra insertable portion 20 and a non-insertable portion 30. Insertable portion 20 commences at a catheter tip 14 and ends at an insertion stop location 25, adjacent non-insertable portion 30.

Catheter tip 14 is completely enclosed within sheath 40. No introducer or tip cover is provided. In different embodiments, an introducer or tip cover may be provided on tip 14 and inside sheath 40. In such embodiments, the introducer or tip cover may be completely removable from tip 14 (e.g., removable in a "breakaway" fashion) and/or be configured to slide along catheter 10 from tip 14 toward insertion stop location 25 thereby extending insertable portion 20. Such an introducer may comprise any suitable device including without limitation an introducer similar to that shown in FIG. 1A, an O'Neil® type introducer (e.g. FIG. 2A), or the like.

Referring again to FIG. 3A, sheath 40 comprises a first sheath terminus 44 and a second sheath terminus 42. First sheath terminus 44 extends beyond tip 14 and completely encloses and protects tip 14. Second sheath terminus 42 is coupled to catheter 10 at attachment point 43. Attachment point 43 is provided between tip 14 and distal end 12. Second sheath terminus 42 slidingly engages catheter 10 about attachment point 43. In the embodiment shown in FIGS. 3A-3C, attachment point 43 is proximal takeoff port 17, however, in different embodiments (e.g., FIG. 4B), attachment point 43 may be distal to takeoff port 17. In still other embodiments, second sheath terminus 42 may comprise a collar that slidingly engages or is fixed to catheter 10 (e.g., FIG. 4C).

A fixation tab 60 extends from distal end 12, distal to takeoff port 17. In general, fixation tab 60 serves to couple catheter 10 to the patient once tip 14 is properly positioned in the patient's bladder. Fixation tab 60 is discussed in more detail below.

Sheath 40 encloses all, or at least part of, insertable portion 20, thereby creating a sheath lumen 41 between sheath 40 and catheter 10. Sheath 40 may comprise any suitable material (e.g., flexible plastic material, flexible fabric material, or the like). Further, sheath 40 and lumen 41 may comprise any suitable geometry including without limitation, rectangular, cylindrical, flattened, inflated, partially inflated, or combinations thereof.

Figure 3B:
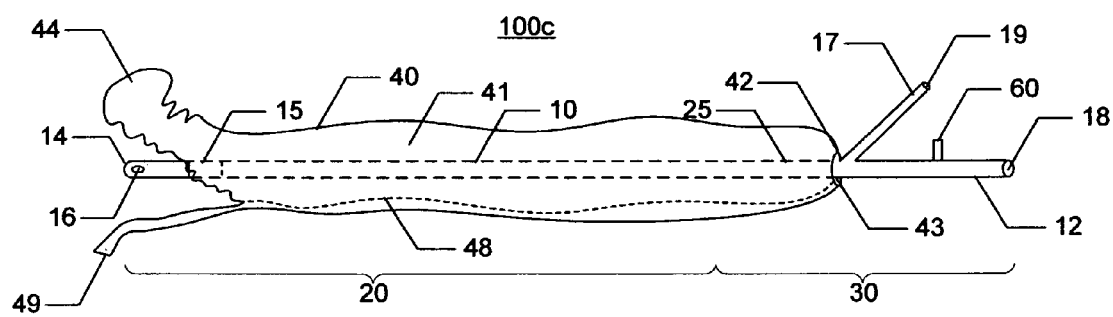
FIG. 3B is a side view of the sheathed indwelling catheter assembly of FIG. 3A, with the sheath partially gathered and partially removed.
Figure 3C:
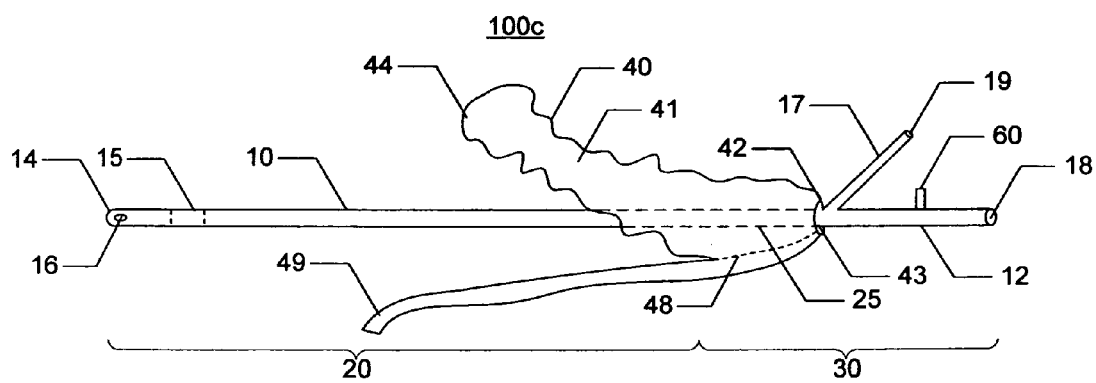
FIG. 3C is a side view of the sheathed indwelling catheter assembly of FIG. 3A, with the sheath substantially gathered and substantially removed.

In the embodiment shown in FIGS. 3A-3C, sheath 40 further comprises a pull tab 49 associated with a tear line 48. Pull tab 49 may be provided in any suitable location. However, preferably pull tab 49 is positioned at the proximal end of sheath 40. Tear line 48 may be a pre-weakened (e.g., very thin, slightly perforated, etc.) line along sheath 40 that is intentionally designed to tear under a force before any other region of sheath 40 tears under the force. In particular, tear line 48 is intended to tear as pull tab 49 is pulled away from sheath 40. By enclosing insertable portion 20, sheath 40 is provided to protect catheter 10 from contamination prior to and during use.

As discussed above, the urethra-insertable portion 20 of catheter 10 is generally the length of catheter that may be appropriately inserted into the patient's urethra in order to perform a successful catheterization to drain the patient's urinary bladder. In embodiments in which an introducer is slid along catheter 10 towards distal end 12 to extend insertable portion 20, the length of the insertable portion 20 may be effectively decreased, at least to some extent, by the distance on catheter 10 required to accommodate such an introducer or tip cover. Further, in embodiments in which sheath 40 is gathered and not removed from catheter 10, the length of the insertable portion 20 may be additionally decreased, at least to some extent, by the distance on catheter 10 required to accommodate gathered sheath 40. However, in the embodiments shown in FIGS. 3A-3C, no introducer or tip cover is provided, and further, sheath 40 is removable from catheter 10. Thus, in the embodiment illustrated in FIGS. 3A-3C, the length of catheter 10 that serves as insertable portion 20 is not decreased by sheath 40 or an introducer or other tip cover.

As discussed above, in some embodiments, lumen 41 of sheath 40 may contain a lubricant or wetting agent in the case of a hydrophilic indwelling catheter. Further, in some embodiments, a sterile lubricating gel may be applied to tip 14 and a proximal portion of insertable portion 20.

Still referring to FIGS. 3A-3C, during use, a nurse may grasp catheter 10 through sheath 40 and exert a force on pull tab 49 to slightly tear sheath 40 along tear line 48 near tip 14, such that tip 14 is exposed from sheath 40, as best seen in FIG. 3B. Still holding catheter 10 through sheath 40, the nurse may align tip 14 with the patient's urethra. The nurse may then begin advancing catheter tip 14 into the patient's urethra. As the catheter tip 14 is advanced by the nurse, a portion of sheath 40 may become gathered toward second sheath terminus 42. At some point, preferably when insertable portion 20 is ⅓ to ½ the way inserted into the patient, the nurse may again pull pull tab 49 to further tear sheath 40 along tear line 48 as best illustrated in FIG. 2C. By appropriately repositioning the nurse's grasp on catheter 10 through sheath 40, and continuing to gently urge the insertable-portion 20 of catheter 10 into the patient's urethra, sheath 40 may continue to be gathered toward collar 46. Periodically, the nurse may further tear sheath 40 along tear line 48 by pulling pull tab 49. When the catheter tip enters the patient's bladder a sufficient distance to commence optimal draining of accumulated urine (e.g., about 1 cm), further insertion of insertable portion 20 ceases. The nurse may then inflate expander 15 by injecting a fluid (e.g., sterile water, saline solution) into port bore 19 provided in takeoff port 17. If sheath 40 has not been completely removed by this point, the remainder of sheath 40 may be completely torn and removed from catheter 10. Further, once tip 14 is properly positioned within the patient's bladder and sheath 40 is completely removed from catheter 10, distal end 12 may be secured to the patient's inner thigh.

Thus, sheath 40 is intended to prevent contamination of insertable portion 20 of indwelling catheter 10 prior to and during use. For example, before use, sheath 40 completely encloses insertable portion 20 of catheter 10. In addition, during use, sheath 40 is partially removed and pulled back by the nurse as insertable portion 20 is advanced into the patient, without the need for the nurse to directly contact insertable portion 20. By deterring contamination, sheath 40 may reduce the occurrences of urinary tract infections in patients. Further, by using sheath 40 to maintain a sterile catheter, the need for separate antiseptic solutions, cotton balls, forceps and other items conventionally used to sterilize an indwelling catheter may be eliminated. By eliminating these additional items required to maintain sterility of an indwelling catheter, embodiments of the sheathed indwelling catheter assembly described herein are intended to reduce the cost for indwelling catheter kits, reduce the time required to perform an indwelling catheterization, and reduce urinary tract infections.

If pressure build-up within lumen 41 is a concern, vents in fluid communication with lumen 41 and the environment outside sheath 40 may be provided.

Referring now to FIGS. 4A-G, partial views of alternative embodiments of a sheathed indwelling catheter assembly are shown. In general, the sheathed indwelling catheter assembly (e.g., assembly 100d, 100e, 100f, 100g, 100h, 100i, 100j) comprises a flexible indwelling catheter 10 and a protective sheath 40. Further, indwelling catheter 10 includes a takeoff port 17, a distal end 12, an insertable portion 20, and a non-insertable portion 30. In some embodiments, takeoff port 17 is positioned adjacent distal end 32. Further, takeoff port 17 includes a port bore 19 that provides fluid communication to an expander (not shown in FIGS. 4A-G) at the proximal end of catheter 10.

Sheath 40 comprises a first sheath terminus (not shown in FIGS. 4A-G) and a second sheath terminus 42 that is coupled to catheter 10 at attachment point 43. Sheath 40 encloses all, or at least part of, the insertable portion 20 within a lumen 41. Sheath 40 may comprise any suitable material including without limitation flexible plastic or the like.

As discussed above, the length of insertable portion 20 may vary depending on a variety of factors including without limitation, the application of catheter 10 (e.g., child, adult), any space required to accommodate an introducer, if provided, that is slid toward second sheath terminus 42, any space required to accommodate sheath 40 if sheath 40 is gathered to continue advancing catheter 10, or combinations thereof.

Figure 4A:
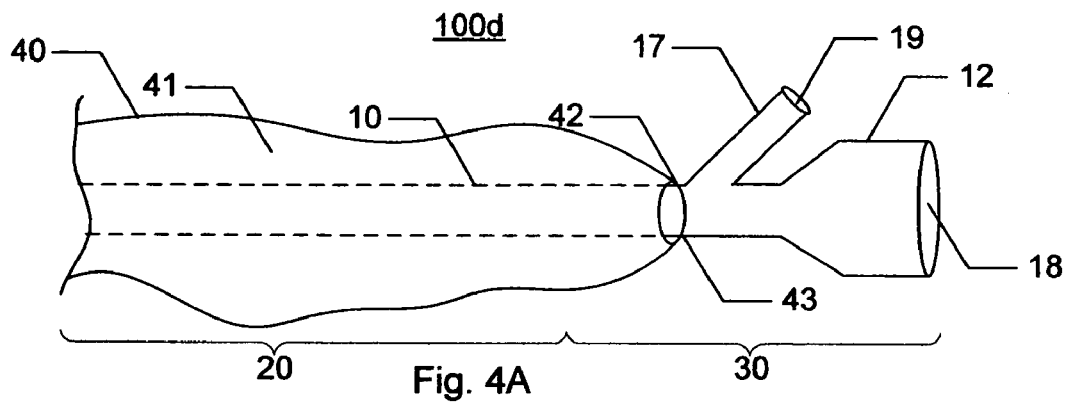
FIG. 4A is a partial side view of another embodiment of a sheathed indwelling catheter assembly.

Referring to FIG. 4A, second sheath terminus 42 is coupled to catheter 10 at attachment point 43. In this embodiment, second sheath terminus 42 slidingly engages catheter 10 about attachment point 43. In different embodiments, second sheath terminus 42 may be fixed to catheter 10 at attachment point 43 such that second sheath terminus 42 does not move rotationally or translationally relative to catheter 10. In addition, in the embodiment illustrated in FIG. 4A, attachment point 43 and second sheath terminus 42, are proximal takeoff port 17 (e.g., second sheath terminus 42 is between the proximal end of catheter 10 and takeoff port 17). In different embodiments, second sheath terminus 42, and attachment point 43, may be coupled to catheter 10 at other locations.

Figure 4B:
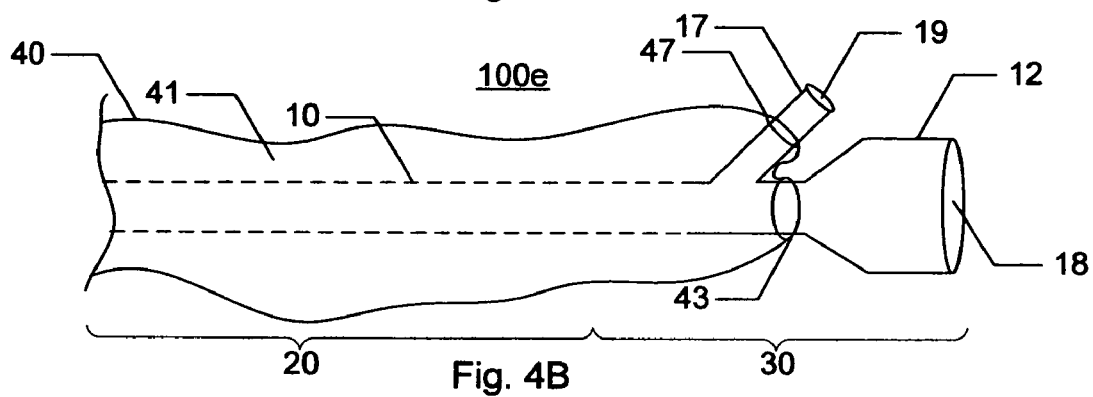
FIG. 4B is a partial side view of another embodiment of a sheathed indwelling catheter assembly.

Referring to FIG. 4B, sheath 40 comprises second sheath terminus 42 and a sheath port terminus 47. Second sheath terminus 42 is coupled to catheter 10 at attachment point 43, and sheath port terminus 47 is coupled to takeoff port 17. In this embodiment, second sheath terminus 42 slidingly engages catheter 10 about attachment point 43, and sheath port terminus 47 slidingly engages takeoff port 17. In different embodiments (e.g., FIG. 4D), second sheath terminus 42 may be fixed to catheter 10 at attachment point 43, while sheath port terminus 47 may slidingly engage takeoff port 17. Further, in other embodiments (e.g., FIG. 4F), second sheath terminus 42 may be fixed to catheter 10 at attachment point 43 and sheath port terminus 47 may be fixed to takeoff port 17. Still further, in select embodiments, second sheath terminus 42 may slidingly engage catheter 10 at attachment point 43 while sheath port terminus 47 may be fixed to takeoff port 17.

Still referring to FIG. 4B, attachment point 43, and second sheath terminus 42, are distal to takeoff port 17 (e.g., second sheath terminus 42 is between takeoff port 17 and distal end 12). In this configuration, even though second sheath terminus 42 and port sheath terminus 47 slidingly engage catheter 10, by coupling both takeoff port 17 and catheter 10 at attachment point 43, sheath 40 may not be easily slid off and removed from catheter 10 without tearing sheath 40.

Figure 4C:
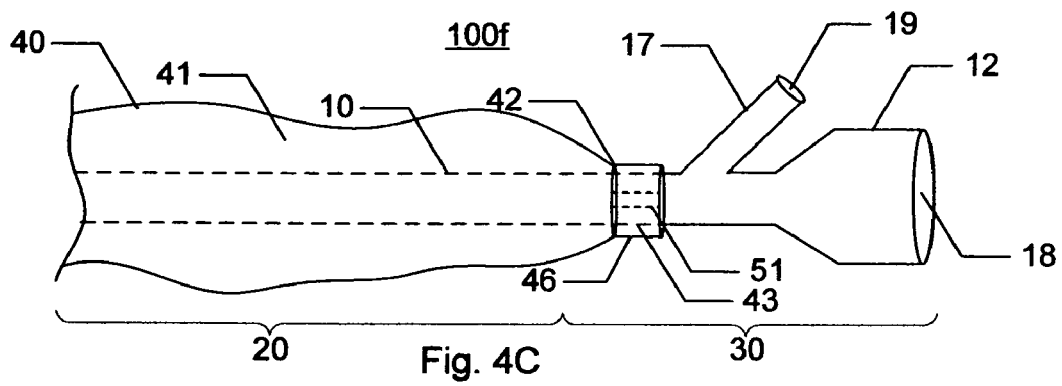
FIG. 4C is a partial side view of another embodiment of a sheathed indwelling catheter assembly.

Referring to FIG. 4C, second sheath terminus 42 is coupled to catheter 10 at attachment point 43. In this embodiment, second sheath terminus 42 is fixed to catheter 10 about attachment point 43 by a second collar 46 such that second sheath terminus 42 and second collar 46 do not move rotationally or translationally relative to catheter 10. In addition, attachment point 43, second sheath terminus 42, and second collar 46 are proximal takeoff port 17 of catheter 10 (e.g., second sheath terminus 42 is between the proximal end of catheter 10 and takeoff port 17). In different embodiments (e.g., FIGS. 4D and 4F), second sheath terminus 42, attachment point 43, and collar 46 may be coupled to catheter 10 at other locations (e.g., distal takeoff port 17).

In addition, second collar 46 illustrated in FIG. 4C includes at least one vent 51 that is in fluid communication with lumen 41 and the environment outside lumen 41. The at least one vent 51 is, in this embodiment, a passageway or duct extending through collar 46 so as to provide relief for potential pressure build-ups within lumen 41.

Figure 4D:
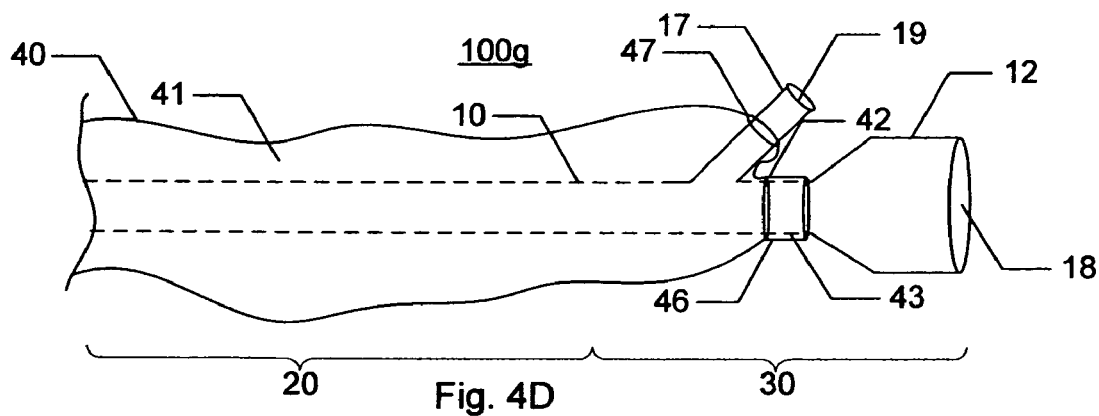
FIG. 4D is a partial side view of another embodiment of a sheathed indwelling catheter assembly.

Referring to FIG. 4D, second sheath terminus 42 is coupled to catheter 10 at attachment point 43 and sheath port terminus 47 is coupled to takeoff port 17. In this embodiment, second sheath terminus 42 is fixed to catheter 10 at attachment point 43 by second collar 46. However, sheath port terminus 47 slidingly engages takeoff port 17. In different embodiments (e.g., FIG. 4B), second sheath terminus 42 may slidingly engage catheter 10 at attachment point 43. Further, in other embodiments (e.g., FIG. 4F), sheath port terminus 47 may be fixed to takeoff port 17.

Still referring to FIG. 4D, second collar 46, attachment point 43, and second sheath terminus 42 are distal takeoff port 17 (e.g., second sheath terminus 42 is between takeoff port 17 and distal end 12). By coupling to both takeoff port 17 and catheter 10 at attachment point 43, sheath 40 may not be easily removed from catheter 10 without tearing sheath 40.

Figure 4E:
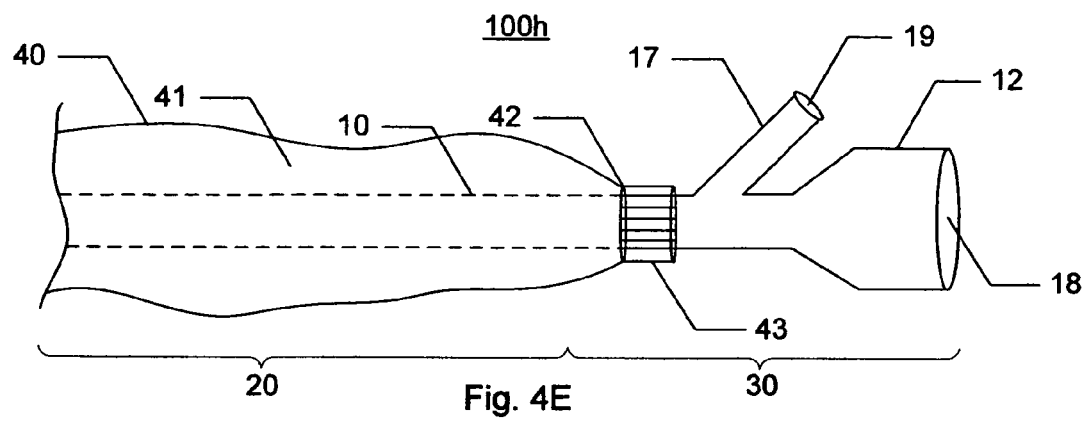
FIG. 4E is a partial side view of another embodiment of a sheathed indwelling catheter assembly.

Referring to FIG. 4E, second sheath terminus 42 is coupled to catheter 10 at attachment point 43. In this embodiment, second sheath terminus 42 is fixed to catheter 10 about attachment point 43 by heat pressing second sheath terminus 42 to catheter 10. In addition, attachment point 43 and second sheath terminus 42 are proximal takeoff port 17 of catheter 10 (e.g., second sheath terminus 42 is between the proximal end of catheter 10 and takeoff port 17). In different embodiments, second sheath terminus 42 may be heat pressed to catheter 10 at other locations (e.g., distal takeoff port 17).

Figure 4F:
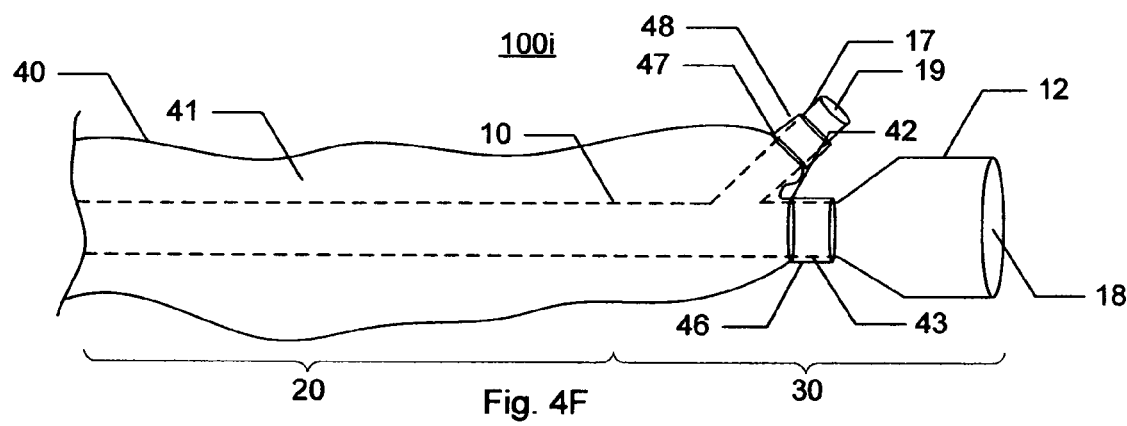
FIG. 4F is a partial side view of another embodiment of a sheathed indwelling catheter assembly.

Referring to FIG. 4F, second sheath terminus 42 is coupled to catheter 10 at attachment point 43 and sheath port terminus 47 is coupled to takeoff port 17. In this embodiment, second sheath terminus 42 is fixed to catheter 10 at attachment point 43 by second collar 46. Further, sheath port terminus 47 is fixed to takeoff port 17 by port collar 48. By coupling to both takeoff port 17 and catheter 10 at attachment point 43, sheath 40 may not be easily removed from catheter 10 without tearing sheath 40.

Figure 4G:
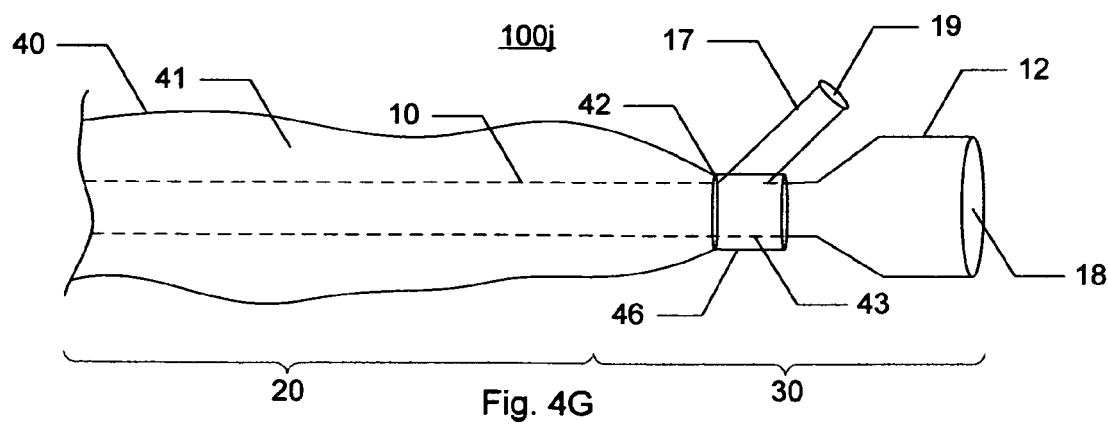
FIG. 4G is a partial side view of another embodiment of a sheathed indwelling catheter assembly.

Referring to FIG. 4G, second sheath terminus 42 is coupled to catheter 10 at attachment point 43. In this embodiment, second sheath terminus 42 is fixed to catheter 10 about attachment point 43 by a second collar 46. In addition, second collar 46 straddles takeoff port 17, such that second sheath terminus 42 is not free to move relative to catheter 10. By straddling takeoff port 17, sheath 40 may not be easily removed from catheter 10 without tearing sheath 40.

In each embodiment disclosed herein, a sheath 40 is provided to partially or completely enclose and protect insertable portion 20 of catheter 10. In particular, sheath 40 is provided to deter contamination of insertable portion 20 by preventing non-sterile surfaces from coming into contact with insertable portion 20.

In some embodiments (not illustrated), the sheathed indwelling catheter assembly (e.g., assembly 100a-j), may further comprise a urine collection bag or receptacle. The urine collection receptacle may be removably attached, permanently attached (non-removable), or integral with the sheathed indwelling catheter assembly. Such a collection receptacle may be constructed of any suitable material. Collection receptacle is preferably made of a flexible, waterproof material (e.g., plastic) and is sized to hold a sufficient volume of urine between periodic emptying of the receptacle. For example, the urine collection receptacle may have a volume in the range of 700-2000 mL.

As previously discussed, in certain embodiments, the sheathed indwelling catheter assembly (e.g., assembly 100a-j) may include a lubricant to lubricate tip 14 and insertable portion 20 prior to entry into the patient's urethra. Such lubricant may be provided within the sheath lumen 41, in an introducer (if provided), in a tip cover, or may be manually applied. Further in some embodiments, the indwelling catheter may be a hydrophilic indwelling catheter that is lubricated by a wetting agent. Such a wetting agent may be provided in the sheath lumen, in an introducer (if provided), in a tip cover, or manually applied. Preferably, at least tip 14 and a proximal $\frac{1}{3}^{rd}$ portion of insertable portion 20 are lubricated prior to advancement into the patient's urethra. In some embodiments, catheter 10 may be pre-lubricated by a sterile gel. House I and House II disclose some embodiments of sheathed catheter assemblies including lubricants and/or wetting agents. In addition to a lubricating agent, in some embodiments, the indwelling catheter used in the sheathed indwelling catheter assembly may be coated with an bacteriostatic and/or bactericidal agent. Without being limited by theory, by providing a bacteriostatic or bactericidal agent on the indwelling catheter, urinary tract infections may be reduced.

In the embodiment illustrated in FIGS. 1A-1C, a plurality of vents 50 are provided in sheath 40 to aid in relieving a possible pressure build-up within lumen 41. As previously discussed, in some indwelling catheter assemblies, the process of gathering sheath 40 to advance insertable portion 20 may result in an increase in pressure (e.g., a pressure build-up) in sheath lumen 41. This may particularly be a problem with indwelling catheter assemblies in which there is limited or no means to relieve pressure build-up within lumen 41 (e.g., no fluid communication between lumen 41 and the environment outside sheath 40). Thus, by including one or more vents (e.g., vents 50 in FIGS. 1A-1C, vent 51 in FIG. 4C) in fluid communication with lumen 41 of sheath 40 and an environment outside sheath 40, some pressure build-up within lumen 41 may be relieved. In certain embodiments, the vents may place lumen 41 of sheath 40 in fluid communication with the lumen of a urine collection receptacle.

Vents 50 illustrated in FIGS. 1A-1C are slits in sheath 40 located adjacent second sheath terminus 42. The at least one vent 51 illustrated in FIG. 4C is a passageway provided through and across second collar 46. However, in general, one or more vents to relieve pressure within lumen 41 may be of any suitable geometry including without limitation, slits, holes, perforations, or combinations thereof. Further, vents to relieve pressure within lumen 41 may be located in any suitable location including without limitation, along the entire sheath 40, at the distal end of sheath 40, at the proximal end of sheath 40, in second collar 46, in an introducer (e.g., introducer 75a in FIGS. 1A-1C), or combinations thereof. To minimize potential contamination of insertable portion 20, any vents are preferably located adjacent second sheath terminus 42 in the region of non-insertable portion 30. Still further, the vents may be of any suitable size that allows adequate pressure relief to lumen 41. However, preferably the vents are small enough to minimize the possibility of insertable portion 20 from contacting a non-sterile surface. U.S. Provisional Application EV 303424660 US (House IV) discloses some embodiments of a vented sheath that may be modified and adapted for use on indwelling catheter 10 of the present disclosure.

FIGS. 1A-1C show the urethra-contacting end of indwelling catheter assembly 100a (proximal end of assembly 100a) as including an introducer 75a. In particular, introducer 75a illustrated in FIGS. 1A-1C is an introducer similar to that disclosed in House II. Further, FIGS. 2A-2C show the urethra-contacting end of indwelling catheter assembly 100b (proximal end of assembly 100b) as including an introducer 75b. In particular, introducer 75b is an O'Neil® type introducer with a "cross-cut" proximal end. However, in general, the proximal end of the sheathed indwelling catheter assembly (e.g., assemblies 100a-j) may comprise any suitable configuration. For example, in some embodiments, the introducer (e.g., 75a in FIG. 1A, 75b in FIG. 2A) may be replaced with another type of protective tip cover adapted keep at least tip 14 the catheter sterile prior to and during use. The introducer or tip cover may be similar to those that are known in the art. Additional suitable configurations for the proximal end of catheter 10 are disclosed in House I, House II, and House III.

Further, in some embodiments (e.g., FIGS. 3A-3C), no introducer or tip cover is provided. In such embodiments, sheath 40 may completely or partially enclose tip 14 and insertable portion 20 of catheter 10 to deter contamination of insertable portion 20.

Still further, in some embodiments, the introducer (e.g., introducer 75a in FIG. 1A, introducer 75b in FIG. 2A) or other tip cover may be completely removable from catheter 10. For example, in some embodiments, the introducer or tip cover may be designed to be broken away from catheter 10 by a user.

In the embodiments of the sheathed indwelling catheter assembly illustrated in FIGS. 1A-1C, 2A-2C, and 3A-3C (assemblies 100a, 100b, and 100c, respectively), a fixation tab 60 is provided. Generally, fixation tab 60 may be used to couple catheter 10 to the patient (e.g., to patient's inner thigh, to patient's lower abdomen, to patient's outer thigh, etc.) once tip 14 of catheter 10 is properly positioned in the patient's urinary bladder. Fixation tab 60 may be coupled to the patient by any suitable means including without limitation, adhesive pad, hook and loop material, an elastic band around the patient's leg that holds the catheter down, or combinations thereof. For example, in some embodiments, fixation tab 60 may include a male or female connector that removably attaches with a mating female or male connector provided on the adhesive pad that is adhered to the patient.

In addition, in other embodiments, catheter 10 may be coupled to the patient via an adhesive pad similar to a Statlock® type pad that includes a removable, releasable, and replaceable clamping mechanism to clamp around a portion of catheter 10.

In embodiments in which an adhesive pad is used (e.g., Statlock® type device) to couple catheter 10 to the patient, preferably catheter 10 is removably coupled to the patient such that the adhesive pad may be changed if it becomes wet or soiled.

In FIGS. 1A-1C, fixation tab 60 is positioned on introducer 75*a*; in FIGS. 2A-2C, fixation tab 60 is provided on introducer 75*b*; in FIGS. 3A-3C, fixation tab 60 is provided on distal end 12. However, in general, fixation tab 60 may be provided at any suitable location on the sheathed indwelling catheter assembly (e.g., assembly 100*a*), such that the indwelling catheter (e.g., indwelling catheter 10) may be coupled to the patient during extended catheterizations. For instance, fixation tab 60 may be provided on distal end 32, on catheter 10 distal to takeoff port 17, on catheter 10 proximal to takeoff port 17, on takeoff port 17, on an introducer (e.g., introducer 75*a* or 75*b*), on a collar coupling sheath 40 to the indwelling catheter, or combinations thereof. Further, in some embodiments, no fixation tab 60 is provided. Still further, in other embodiments (e.g., FIG. 2A), more than one fixation tab 60 may be provided.

During extended use of the indwelling catheter 10, both expander 15 and fixation tab 60 may cooperate to deter withdraw of indwelling catheter 10 from the patient and to prevent excessive movement of indwelling catheter 10 relative to the patient.

In general, distal end 12 of indwelling catheter 10 may comprise any suitable geometry. Examples of suitable geometries include without limitation, flared or increased diameter distal end 12 (e.g., FIGS. 1A-1C, 4A-4G), uniform diameter distal end 12 (e.g., FIGS. 2A-2C, 3A-3C), decreasing diameter distal end 12, etc.

Further, in each of the Figures disclosed herein, distal end 12 of catheter 10 extends outside sheath 40. However, in other embodiments, part or all of non-insertable portion 30, including distal end 12, may be enclosed by sheath 40, similar to those shown in House III, which discloses catheter assemblies in which non-insertable portion 30 is partially and completely enclosed by sheath 40.

Embodiments of the sheathed indwelling catheter assembly disclosed in FIGS. 2A-2C and 3A-3C (assemblies 100*b* and 100*c*, respectively), include a removable sheath 40. Sheath 40 includes a pre-weakened tear line 48 coupled to a pull tab 49 such that sheath 40 is designed to tear along tear line 48 when pull tab 49 is pulled. Other embodiments of the sheathed indwelling catheter assembly (e.g., 100*a*, and *d-j*) may include a removable sheath 40 similar to that shown in FIGS. 1A-1C and 3A-3C. Such a removable sheath may be configured to be completely removed once tip 14 of indwelling catheter 10 is properly positioned in the patient urinary bladder or removed as tip 14 is advanced into the patient's urethra. Preferably, any removable sheath is removed in a manner to minimize opportunities for insertable portion 20 to contact a non-sterile surface.

Catheterization Kit

Figure 5:
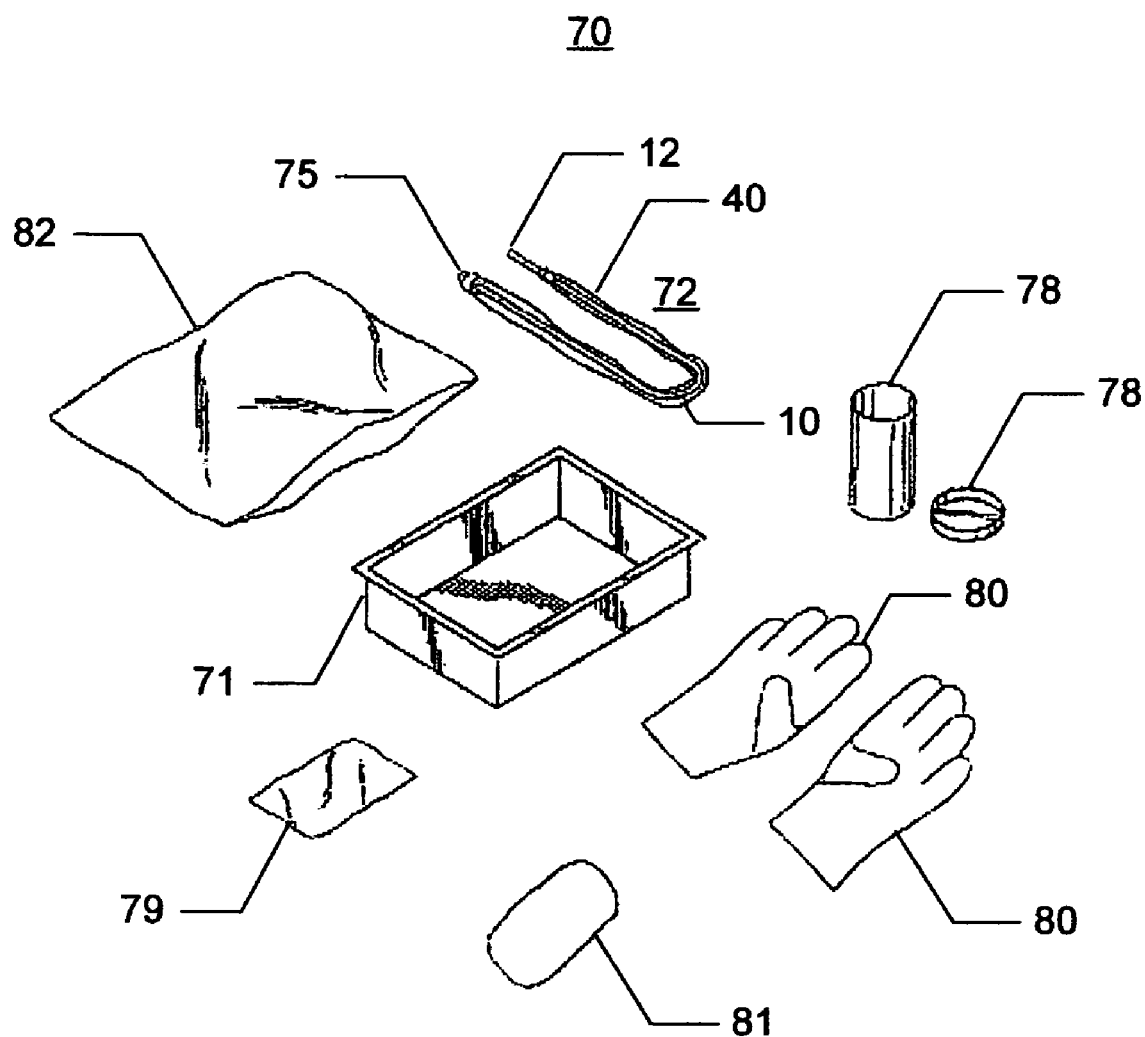
FIG. 5 shows the contents of an indwelling catheterization kit according to an embodiment of the present invention.

Referring to FIG. 5, a representative catheterization kit ("cath kit") 70 that is particularly useful for long-term patient catheterizations includes a sheathed indwelling catheter assembly 72, representative of those shown and described above as sheathed catheter assemblies 100*a-j*. For example, sheathed catheter assembly 72 may include an introducer 75, catheter 10, and a sheath 40. Sheath 40 may be coupled to introducer 75, if present, and coupled to catheter 10 near the distal end 12 of catheter 10. Further, assembly 72 may include one or more vents (not shown in FIG. 5) in any suitable location including without limitation, in sheath 40, in introducer 75, in a collar (e.g., collar 43) coupling sheath 40 to catheter 10, or combinations thereof.

In addition to the sheathed catheter assembly, the kit preferably also contain one or more packaged antiseptic swabs 79 (e.g., swabs saturated with Betadine, Povidone-Iodine or other suitable antiseptic), disposable gloves 80, an adhesive pad 81 (e.g., Statlock® type adhesive pad) small urine specimen bottle (with cap) 78, and a tray 71 that holds these supplies and also serves as a urine collection container and has a capacity in the range of 700-2000 mL, preferably about 1000 mL. Preferably a fenestrated drape is also included in the kit. A gauze pad may also be included in the kit as a convenient wipe at the end of the procedure. The kit components are protected by a sanitary wrapper or cover 82. All kit components are preferably disposable.

Absent from the present kit, however, are the customary liquid antiseptic packet, cotton balls, tray for cotton balls, forceps, and packet containing lubricating jelly. In some embodiments, the fenestrated drape is also omitted from the kit without compromising sterile technique. The conventional waterproof absorbent pad is also unnecessary, as it was often included in the past primarily to provide a sterile field for placement of the sterile jelly. Preferably, the lubricant is provided within the indwelling catheter assembly. For example, a lubricating amount of sterile lubricant may be present inside the sheath lumen, or inside introducer 75. Further, in some embodiments, indwelling catheter 10 may be a lubricated hydrophilic type as is known in the art, in which case the lumen and/or the introducer 75 (e.g., an introducer) a wetting agent (e.g., water). A drawback of conventional apparatus and methods is that contact between the indwelling catheter and any non-sterile surface (e.g., nurses hands, patient's leg, etc.), as when lubricating jelly is applied, for instance, increases the risk of contamination of the indwelling catheter, which may result in a urinary tract infection. In contrast, with the present kit, if sheathed indwelling catheter assembly 72 touches anything outside the sterile field, the insertable portion of the catheter remains sterile. Another potential problem associated with conventional catheterization kits and procedures is that, if a glove touches anything outside the sterile field and then touches the catheter, the catheter may become contaminated. If a sheathed indwelling catheter assembly is employed instead, and if a glove becomes contaminated, the indwelling catheter nevertheless remains sterile inside the protective sheath. Thus, the risk of infection and patient morbidity is reduced or eliminated with use of the new catheterization kit and catheterization procedure.

Liquid antiseptic packet, cotton balls, tray for cotton balls, forceps, and packet containing lubricating jelly are not needed for carrying out a streamlined catheterization procedure with the above-described sheathed catheter assembly 72 and maintaining sterile technique.

Catheterization Procedure

Embodiments of the sheathed indwelling catheter assembly of the present disclosure (e.g., assemblies 100*a-j*) may be used alone or as part of catheterization kit 70. In general, the sheathed indwelling catheter assembly is employed as described above in reference to FIGS. 1A-1C, 2A-2C, and 3A-3C.

When the sheathed indwelling catheter assembly (e.g., assembly 100*a-j*) is included as part of the catheterization kit 70, catheterization kit 70 is preferably employed as follows: After opening the sanitary wrapper 82, the nurse dons the gloves 80 and places the fenestrated drape, if provided, around the patient's genitalia. The packet 79 containing the antiseptic swabs is opened and the urethral area around the urethral opening is cleansed using the antiseptic swabs. Then an embodiment of the sheathed indwelling catheter assembly of the present invention (e.g., 100*a*, 100*b*, 100*c*) may be inserted into the patient's urethra and advanced to the patient's urinary bladder in the manner previously described in reference to FIGS. 1A-1C, 2A-2C, or 3A-3C.

When the catheter tip enters the patient's bladder a sufficient distance to commence optimal draining of accumulated urine (e.g., 1 cm), further insertion ceases. At about the same time, the nurse may inject fluid through port bore 19 of takeoff port 17 to inflate expander 15, thereby maintaining indwelling catheter 10 in the appropriate position for extended catheterization. Further, catheter 10 may be coupled to the patient by applying adhesive pad 81 to the patient and coupling catheter 10 to the adhesive pad. For example, if adhesive pad 81 is similar to a Statlock® type adhesive pad, the adhesive pad 81 may be adhered to the patient and catheter 10 may be coupled to adhesive pad 81 by a removable, releasable, and replaceable locking device provided in the pad.

Prior to commencement of urine drainage, the distal end 12 is coupled to tray 71 so that urine can drain into tray 71 while preventing catheter 10 from contacting the collected urine. Alternatively, any other suitable urine receptacle may be used instead of the disposable tray 71 provided as part of the kit. In some embodiments, a urine receptacle or bag may already be integral with or otherwise attached to distal end 12.

After commencement of urine flow, outlet 18 of catheter 10 may be directed briefly into the specimen container 78, to collect a sterile specimen, if needed. Upon completion of urine evacuation, catheter 10 may be maintained in proper position within the patient for long-term catheterization. In particular, indwelling catheter assembly 72 may be maintained in proper position within the patient for an extended period of time by expander 15 and fixation tab 60. The entire catheterization process can usually be accomplished by a nurse in a relatively short period of time, maintaining sterile technique throughout the procedure. Once the catheterization is no longer necessary, expander 15 may be deflated and catheter 10 may be simply withdrawn from the urethra and disposed. If desired, the catheter may be retracted into the sheath prior to disposal The disclosed catheterization kit 70 and simplified procedure offers a way to simplify and streamline long-term or extended catheterization procedures without compromising sterile technique. Every item that the new kit 70 eliminates from the customary indwelling catheterization setup will decrease the number of procedural steps, and also reduces the amount of nursing time needed. Fewer steps also reduces the patient's risk for urinary tract infection, and decreases inconvenience for the patient. Kit 70 is intended to substantially reduce nursing time required to carry out an indwelling catheterization procedure.

The embodiments described herein are intended to offer the potential to improve the convenience and sterility desirable for catheterization procedures. Some embodiments are designed to deter contamination of an indwelling catheter, while streamlining the procedures required to employ the indwelling catheter. By deterring contamination of the indwelling catheter, embodiments of the present invention reduce the potential for urinary tract infections. Further, by streamlining the indwelling catheterization procedure, the embodiments disclosed herein are intended to reduce the time required to employ an indwelling catheter while maintaining a sterile environment.

The disclosures of all patents, patent applications, and publications cited herein are hereby incorporated herein by reference in their entirety, to the extent that they provide exemplary, procedural, or other details supplementary to those set forth herein. Further, the discussion of a reference in this disclosure is not an admission that it is prior art to the present invention, especially any reference that may have a publication date after the priority date of this application.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An indwelling urinary catheter assembly comprising:
an indwelling catheter comprising a first end having a urine inlet, a second end having a urine outlet, a takeoff port having a port bore, an expander, and a urethra insertable portion;
wherein the urine inlet and urine outlet are in fluid communication with one another and wherein the port bore and the expander are in fluid communication with one another;
a pliable sheath comprising a lumen, wherein the sheath encloses at least a portion of the insertable portion; and
an introducer attached to the sheath, wherein the introducer is dimensioned and configured to enclose and support the first end when in an initial position, the introducer slidingly receives the insertable portion during insertion of the insertable portion into the urethra of a patient, wherein the introducer is dimensioned and configured to be partially inserted into the urethra of a patient, and the introducer together with the sheath encloses all of the urethra-insertable portion when in the initial position;
wherein the sheath further comprises a terminus directly coupled to an area of the catheter that includes a portion of the takeoff port; and
wherein the terminus comprises a collar having at least one vent in fluid communication with the lumen and an environment outside the sheath, the vent being dimensioned and configured to relieve a pressure build-up within the sheath.

2. The indwelling catheter assembly of claim 1, wherein the terminus sealingly engages the catheter at an attachment point at the area including the portion of the takeoff port.

3. The catheter assembly of claim 1, further comprising a non-insertable portion, wherein at least part of the non-insertable portion comprises an uncovered region of the indwelling catheter outside the sheath.

4. The catheter assembly of claim 3 further comprising a urine receptacle coupled to the non-insertable portion of the catheter.

5. The indwelling catheter assembly of claim 1, wherein the sheath is removably attached to the indwelling catheter.

6. An catheterization kit comprising:
the indwelling urinary catheter assembly of claim 1; and
a sanitary wrapper enclosing the assembly.

7. The kit of claim 6 consisting essentially of the following items:
the indwelling urinary catheter assembly;
at least one antiseptic swab;
disposable gloves;
a urine specimen container; and
a tray capable of holding the catheter assembly, swab(s), gloves, and specimen container,
wherein the tray is also capable of serving as a urine receptacle; and a
sanitary wrapper enclosing the items.

8. The kit of claim 7 excluding one or more drapes.

9. The kit of claim 8 excluding forceps.

10. The kit of claim 9 excluding antiseptic liquid.

11. The indwelling catheter assembly of claim 1, wherein the indwelling catheter has a total length from the first end to the second end, wherein the indwelling catheter is prelubricated from the first end to a point located at $\frac{1}{3}^{rd}$ the length from the first end.

12. The indwelling catheter assembly of claim 1, wherein the introducer comprises a lubricant reservoir operable to lubricate the insertable portion.

13. The indwelling catheter assembly of claim 1, further comprising a fixation tab coupled to the collar.

14. An indwelling urinary catheter assembly comprising:
an indwelling catheter comprising a first end having a urine inlet, a second end having a urine outlet, a takeoff port between the first end and second end, an expander, and a urethra insertable portion;
wherein the takeoff port includes a port bore in fluid communication with the expander;
wherein the urine inlet and urine outlet are in fluid communication;
a pliable sheath comprising a lumen, wherein the sheath encloses at least a portion of the insertable portion; and
an introducer attached to the sheath opposite the terminus, wherein the introducer is dimensioned and configured to enclose and support the first end when in an initial position, the introducer slidingly receives the insertable portion during insertion of the insertable portion into the urethra of a patient, wherein the introducer is dimensioned and configured to be partially inserted into the urethra of a patient, and the introducer together with the sheath encloses all of the urethra-insertable portion when in the initial position;
wherein the sheath further comprises a terminus directly coupled to an area of the catheter that includes a portion of the takeoff port; and
wherein the terminus comprises a collar having at least one vent in fluid communication with the lumen and an environment outside the sheath, the vent being dimensioned and configured to relieve a pressure build-up within the sheath.

15. The indwelling catheter assembly of claim 14, wherein the sheath is removably attached to the indwelling catheter.

16. The indwelling catheter assembly of claim 15, wherein the collar is dimensioned and configured to removably attach to the introducer.

17. The indwelling catheter assembly of claim 14, wherein the introducer further comprises a fixation tab adapted to couple the catheter to a patient.

18. A catheterization kit comprising:
the indwelling urinary catheter assembly of claim 14; and
a sanitary wrapper enclosing the assembly.

19. An indwelling urinary catheter assembly comprising:
an indwelling catheter comprising a first end having a urine inlet, a second end having a urine outlet, a takeoff port between the first end and second end, an expander, and a urethra insertable portion;
wherein the takeoff port includes a port bore in fluid communication with the expander;
wherein the urine inlet and urine outlet are in fluid communication;
a pliable sheath comprising a lumen and a terminus, wherein the sheath encloses part of the insertable portion, and wherein the terminus is directly coupled to each of an area of the catheter that includes a portion of the takeoff port, the indwelling catheter between the takeoff port and first end, and the indwelling catheter between the takeoff port and the second end, wherein the terminus further comprises a collar having at least one vent in fluid communication with the lumen and an environment outside the sheath, the vent being dimensioned and configured to relieve a pressure build-up within the sheath; and
an introducer attached to the sheath opposite the terminus, wherein the introducer is dimensioned and configured to enclose and support the first end when in an initial position, the introducer slidingly receives the insertable portion during insertion of the insertable portion into the urethra of a patient, wherein the introducer is dimensioned and configured to be partially inserted into the urethra of a patient, and the introducer together with the sheath encloses all of the urethra-insertable portion when in the initial position.

20. The indwelling catheter assembly of claim 19, wherein the sheath is removably attached to the indwelling catheter.

21. The indwelling catheter assembly of claim 19, wherein the collar is dimensioned and configured to attach to the introducer.

22. The indwelling catheter assembly of claim 19, wherein the indwelling catheter is coated with a bacteriostatic or bactericidal agent.

23. A catheterization kit comprising:
the indwelling urinary catheter assembly of claim 19; and
a sanitary wrapper enclosing the assembly.

* * * * *